United States Patent
Yoshitake et al.

(10) Patent No.: US 6,855,746 B2
(45) Date of Patent: Feb. 15, 2005

(54) PROCESS FOR THE PRODUCTION OF MOLDED PARTICLES FOR ENZYME- OR MICROBIAL CELL-IMMOBILIZATION

(75) Inventors: Junya Yoshitake, Hiratsuka (JP); Kenji Miyagawa, Hiratsuka (JP); Kenji Seko, Yokosuka (JP)

(73) Assignee: Kansai Paint Co., Ltd., Hyogo-ken (JP)

( * ) Notice: Subject to any disclaimer, the term of this patent is extended or adjusted under 35 U.S.C. 154(b) by 85 days.

(21) Appl. No.: 10/293,500

(22) Filed: Nov. 14, 2002

(65) Prior Publication Data

US 2003/0100636 A1 May 29, 2003

(30) Foreign Application Priority Data

Nov. 15, 2001 (JP) ........................................ 2001-349536

(51) Int. Cl.$^7$ .................................................. C08F 2/46
(52) U.S. Cl. ............................. 522/84; 522/86; 522/87; 522/88; 522/89; 522/90; 522/96; 522/97; 522/100; 522/103; 522/173; 522/174; 522/179; 522/180; 428/402
(58) Field of Search ............................. 522/84, 86, 87, 522/88, 89, 90, 96, 97, 100, 103, 173, 174, 179, 180

(56) References Cited

U.S. PATENT DOCUMENTS 6,086,795 A * 7/2000 Hatton ........................ 252/582

* cited by examiner

Primary Examiner—James Seidleck
Assistant Examiner—Sanza L. McClendon
(74) Attorney, Agent, or Firm—Wenderoth, Lind & Ponack, L.L.P.

(57) ABSTRACT

This invention provides a process for the production of molded particles for enzyme- or microbial cell-immobilization which is characterized in that:
an aqueous liquid composition which comprises:
(A) an unsaturated group-containing urethane resin which is obtained by making a compound (a) having one hydroxyl group and one epoxy group in a molecule react with a compound (b) having one carboxyl group and one ethylenically unsaturated group in a molecule, and further making thus obtained unsaturated group-containing diol (c) react with polyisocyanate compound (d);
(B) a polymerization initiator; and
(C) water-soluble macromolecular polysaccharides which are capable of gelation by contact with metal ion;
is gelatinized, in an aqueous medium which contains metal ion, to be particulate gel, which is then subjected to photopolymerization and/or thermopolymerization by which to cause the crosslinking reaction of ethylenically unsaturated group in said particulate gel.

20 Claims, No Drawings

PROCESS FOR THE PRODUCTION OF MOLDED PARTICLES FOR ENZYME- OR MICROBIAL CELL-IMMOBILIZATION

BACKGROUND OF THE INVENTION

1. Field of Invention

This invention relates to a process for the production of molded particles for enzyme- or microbial cell-immobilization.

2. Description of Prior Arts

There have been known various methods to immobilize enzymes or microorganisms, such as encapsulation method, physical adsorption method and covalent bond method. Lump-like or sheet-like immobilized matters which are produced by these methods are usually cut or crushed fine before they are applied to enzyme reaction or microbial reaction. In these cases, however, immobilized matters often adhere to one another at the face, which decreases the efficiency of enzyme reaction or microbial reaction. On this account, it has recently been proposed to immobilize enzyme or microorganism cells in the form of molded particles so that they may have less contact area and therefore be readily flowable, and to thereby increase the efficiency of enzyme reaction or microbial reaction [e.g., Japanese Patent Publication No. Sho 62 (1987)-19837, Japanese Patent Application Laid-Open No. Hei 10 (1998)-210969].

Urethane resin which has conventionally been used for immobilizing enzyme or microorganisms has, however, photoreactive group(s) only at molecular terminals. Hence, when said photoreactive groups are subjected to photopolymerization reaction to render the urethane resin high-molecular, the resultant polymer molecules decreases both in the degree of unsaturated bond and in the number of crosslinking points, and thus fails to give molded particles with sufficient strength.

It is the primary objective of this invention to provide a process for the production of molded particles for enzyme- or microbial cell-immobilization which have good mechanical strength.

As a result of assiduous study in order to attain the above-mentioned objective, the inventors of this invention have now found out that, when a compound having one hydroxyl group and one epoxy group in a molecule is made to react with a compound having one carboxyl group and one ethylenically unsaturated group in a molecule, and when thus obtained unsaturated group-containing diol is further allowed to react with polyisocyanate compound, the resultant novel unsaturated group-containing urethane resin, when used as a constituent material for particulate carrier for immobilization, gives molded particles with remarkably much higher mechanical strength than the case where conventional urethane resin is used. The inventors have thus completed this invention.

SUMMARY OF THE INVENTION

According to this invention, there is provided a process for the production of molded particles for enzyme- or microbial cell-immobilization which is characterized in that: an aqueous liquid composition which comprises:

(A) an unsaturated group-containing urethane resin which is obtained by making a compound (a) having one hydroxyl group and one epoxy group in a molecule react with a compound (b) having one carboxyl group and one ethylenically unsaturated group in a molecule, and further making thus obtained unsaturated group-containing diol (c) react with polyisocyanate compound (d);

(B) a polymerization initiator; and
(C) water-soluble macromolecular polysaccharides which are capable of gelation by contact with metal ion;

is gelatinized, in an aqueous medium which contains metal ion, to be particulate gel, which is then subjected to photopolymerization and/or thermopolymerization by which to cause the crosslinking reaction of ethylenically unsaturated group in said particulate gel.

In the following, the process of this invention for the production of molded particles for enzyme- or microbial cell-immobilization is explained in more detail.

DETAILED DESCRIPTION OF THE INVENTION

The molded particles of this invention are produced as follows: an aqueous liquid composition which comprises, as essentially components, (A) an unsaturated group-containing urethane resin, (B) a polymerization initiator and (C) water-soluble macromolecular polysaccharides, is dripped or poured into an aqueous medium which contains metal ion, and is thus gelatinized to be particulate gel, which is then subjected to photopolymerization and/or thermopolymerization by which to cause the reaction and curing of ethylenically unsaturated group in said particulate gel.

Unsaturated Group-containing Urethane Resin (A)

Unsaturated group-containing urethane resin which is component (A) in the above-mentioned aqueous liquid composition is produced by making a compound (a) having one hydroxyl group and one epoxy group in a molecule react with a compound (b) having one carboxyl group and one ethylenically unsaturated group in a molecule, and further making thus obtained unsaturated group-containing diol (c) react with polyisocyanate compound (d).

Compound (a) Having One Hydroxyl Group and One Epoxy Group in a Molecule

Compound (a) which is used for the production of unsaturated group-containing urethane resin (A) is a compound which contains one hydroxyl group and one epoxy group in a molecule. Examples of compound (a) include glycidol and a compound of the following formula (I) or (II):

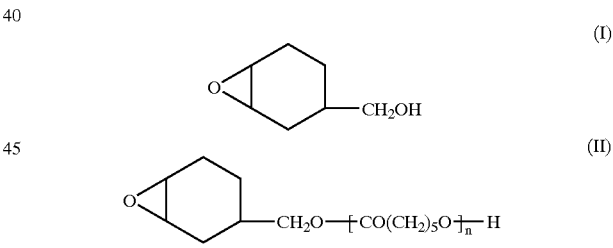

wherein n denotes an integer of 1 to 10, preferably 1 to 3.

These compounds may be used either singly or in combination of two or more species. Among these, glycidol is in particular suitable since it can enhance the concentration of unsaturated groups in unsaturated group-containing urethane resin (A).

Compound (b) Having One Carboxyl Group and One Ethylenically Unsaturated Group in a Molecule Compound (b) which is allowed to react with the above-mentioned compound (a) has one carboxyl group and one ethylenically unsaturated group in a molecule. Examples of compound (b) include acrylic acid, methacrylic acid; ω-carboxy-polycaprolactone monoacrylate, phthalic acid monohydroxyethyl acrylate and acrylic acid dimer (which are available from TOAGOSEI CO., LTD. under trade marks of ARONIX M-5300, ARONIX M-5400 and ARONIX M-5600 respectively); phthalic acid monohydroxyethyl acrylate, phthalic acid monohydroxypropyl acrylate, hexahydrophthalic acid monohydroxypropyl acrylate and tetrahydrophthalic acid monohydroxypropyl acrylate (which are available from OSAKA ORGANIC CHEMICAL INDUSTRY LTD. under trade marks of VISCOAT #2000, VISCOAT #2100, VISCOAT #2150 and VISCOAT #2180 respectively), which are however not restrictive. These compounds may be used either singly or in combination of two or more species. Among these, acrylic acid and methacrylic acid are in particular suitable since they can enhance the concentration of unsaturated groups in unsaturated group-containing urethane resin (A).

Unsaturated Group-containing Diol (c)

Unsaturated group-containing diol (c) is produced by making the afore-mentioned compound (a) having one hydroxyl group and one epoxy group in a molecule react with compound (b) having one carboxyl group and one ethylenically unsaturated group in a molecule react.

The proportion of compound (a) and compound (b) used is not strictly restricted. Generally, however, they are suitably used at such a proportion that the equivalent ratio of epoxy group in compound (a)/carboxyl group in compound (b) may fall within a range of 0.8/1 to 1/0.8, in particular 0.9/1 to 1/0.9.

Reaction between compound (a) and compound (b) may be conducted in the absence of solvent, or in a suitable inert organic solvent such as hydrocarbon-type, ketone-type and ester-type organic solvent, usually at about 60 to about 150° C., in particular at 80 to 120° C., for about one hour to about 48 hours, in particular for about three hours to about 12 hours.

In the above-mentioned reaction, if necessary, there may be used known catalyst for accelerating reaction between epoxy group and carboxyl group. Examples of reaction catalyst include amines such as triethyl amine, and quaternary ammonium salt such as tetrabutylammonium bromide. Said reaction catalyst may be used in an amount of 0.01 to 10 parts by weight, preferably 0.05 to 5 parts by weight, per 100 parts by weight of total solid content of compound (a) and compound (b).

Polyisocyanate Compound (d)

Polyisocyanate compound (d) which is made to react with thus produced unsaturated group-containing diol (c) is a compound which contains at least two isocyanate groups in a molecule. As examples of said polyisocyanate compound, there may be mentioned diisocyanate compound and other polyisocyanate compound, among which diisocyanate compound is suitable.

The above-mentioned diisocyanate compound includes aliphatic, alicyclic and aromatic diisocyanate compounds, concrete examples of which are tolylene diisocyanate, 4,4'-diphenylmethane diisocyanate, 2,4'-diphenylmethane diisocyanate, xylylene diisocyanate, hexamethylene diisocyanate, lysine diisocyanate, 4,4'-methylene-bis (cyclohexylisocyanate), methylcyclohexane-2,4 (or 2,6)-diisocyanate, 1,3-(isocyanatomethyl)cyclohexane, isophorone diisocyanate, trimethylhexamethylene diisocyanate, dimer acid diisocyanate, dianisidine diisocyanate, phenyl diisocyanate, halophenyl diisocyanate, methylene diisocyanate, ethylene diisocyanate, butylene diisocyanate, propylene diisocyanate, octadecylene diisocyanate, 1,5-naphthalene diisocyanate, polymethylene polyphenylene diisocyanate, triphenylmethane triisocyanate, naphthalene diisocyanate, polymer of tolylene diisocyanate, polymer of diphenylmethane diisocyanate, polymer of hexamethylene diisocyanate, 3-phenyl-2-ethylene diisocyanate, cumene-2,4-diisocyanate, 4-methoxy-1,3-phenylene diisocyanate, 4-ethoxy-1,3-phenylene diisocyanate, 2,4'-diisocyanate diphenylether, 5,6-dimethyl-1,3-phenylene diisocyanate, 4,4'-diisocyanate diphenylether, benzidine diisocyanate, 9,10-anthracene diisocyanate, 4,4'-diisocyanate benzyl, 3,3'-dimethyl-4,4'-diisocyanate diphenylmethane, 2,6-dimethyl-4,4'-diisocyanate diphenyl, 3,3'-dimethoxy-4,4'-diisocyanate diphenyl, 1,4-anthracene diisocyanate, phenylene diisocyanate, 2,4,6-tolylene triisocyanate, 2,4,4'-triisocyanate diphenylether, 1,4-tetramethylene diisocyanate, 1,6-hexamethylene diisocyanate, 1,10-decamethylene diisocyanate and 1,3-cyclohexylene diisocyanate, which are however not restrictive. These compounds may be used either separately or in combination of two or more species.

Examples of the above-mentioned other polyisocyanate compound include polyisocyanate compound having at least three isocyanate groups such as triphenylmethane-4,4',4"-triisocyanate, 1,3,5-triisocyanatobenzene, 2,4,6-triisocyanatotoluene, 4,4'-dimethyldiphenylmethane-2,2',5, 5'-tetraisocyanate; adduct which is prepared by making polyisocyanate compound react with polyol such as ethylene glycol, propylene glycol, 1,4-butylene glycol, polyalkylene glycol, trimethylol propane and hexanetriol in such a manner that isocynate group is in excess of hydroxy group of the polyol; biuret type- and isocyanuric ring type-adducts of polyisocyanate compound such as hexamethylenediisocyanate, isophorone diisocyanate, tolylene diisocyanate, xylylene diisocyanate, 4,4'-diphenylmethane diisocyanate and 4,4'-methylenebis (cyclohexylisocyanate).

The above-mentioned polyisocyantate compounds may be used either singly or in combination of two or more species.

Especially suitable among these polyisocyanate compounds (d) are tolylene diisocyanate, 4,4'-diphenylmethane diisocyanate, xylylene diisocyanate, hexamethylene diisocyanate, isophorone diisocyanate, trimethylhexamethylene diisocyanate and dimer acid diisocyanate.

Polyol (e)

If necessary, unsaturated group-containing diol (c) may partially be replaced with polyol (e) other than unsaturated group-containing diol (c) for the purpose of introducing ether bond into unsaturated group-containing urethane resin (A) or regulating the amount of ethylenically unsaturated group in unsaturated group-containing urethane resin (A).

Polyol (e) other than unsaturated group-containing diol (c) which is, if necessary, used has at least two alcoholic-and/or phenolic-hydroxyl groups in a molecule. As polyol (e), there may also be used ethylenically unsaturated group-containing polyol other than unsaturated group-containing diol (c).

Examples of the above-mentioned polyol (e) include ethylene glycol, diethylene glycol, triethylene glycol, propylene glycol, dipropylene glycol, polyethylene glycol (molecular weight: at most 6,000), trimethylene glycol, polypropylene glycol (molecular weight: at most 6,000), tetramethylene glycol, polytetramethylene glycol, 1,2-butylene glycol, 1,3-butanediol, 1,4-butanediol, 1,5-pentanediol, neopentyl glycol, 1,2-hexylene glycol, 1,6-hexane diol, heptane diol, 1,10-decane diol, cyclohexane diol, 2-butene-1,4-diol, 3-cyclohexene-1,1-dimethanol, 4-methyl-3-cyclohexene-1,1-dimethanol, 3-methylene-1,5-pentanediol, (2-hydroxyethoxy)-1-propanol, 4-(2-hydroxyethoxy)-1-butanol, 5-(2-hydroxyethoxy)-pentanol, 3-(2-hydroxypropoxy)-1-propanol, 4-(2-hydroxypropoxy)-1-butanol, 5-(2-hydroxypropoxy)-1-pentanol, 1-(2-hydroxyethoxyl)-2-butanol, 1-(2-hydroxyethoxy)-2-pentanol, dimethylolpropionate, dimethylolbutanoate, dimethylolvalerate, bisphenol A hydride, glycerin, polycaprolactone, 1,2,6-hexane triol, trimethylol propane, trimethylol ethane, pentanetriol, tris(hydroxymethyl) aminomethane, 3-(2-hydroxyethoxy)-1,2-propane diol, 3-(2-hydroxypropoxy)-1,2-propane diol, 6-(2-hydroxyethoxy)-1,2-hexane diol, pentaerythritol, dipentaerythritol, mannitol and glucose. In particular suitable are diethylene glycol, triethylene glycol and polyethylene glycol (molecular weight: at most 6,000) in view of hydrophilicity and strength.

Examples of the above-mentioned ethylenically unsaturated group-containing polyol (e) include glycerol mono (meth)acrylate, trimethylolpropane mono(meth)acrylate, pentaerythritol mono(meth)acrylate, dipentaerythritol mono (meth)acrylate, hydroxyisocyanurate mono(meth)acrylate, neopentyl glycolmono(meth)acrylate and pentaerythritol monoallyl ether.

Unsaturated group-containing urethane resin (A) can be produced by subjecting the above-mentioned unsaturated group-containing diol (c), polyisocyanate compound (d) and, if necessary, polyol (e) as well, to urethane-forming reaction by any known method.

The proportion of unsaturated group-containing diol (c), polyisocyanate compound (d) and polyol (e) in said reaction is not strictly restricted, but may be varied in a wide range depending on the degree of saturation and number average molecular weight which finally obtained unsaturated group-containing urethane resin (A) is required to have. Generally, however, the following proportion is appropriate, on the basis of total solid content of unsaturated group-containing diol (c), polyisocyanate compound (d) and polyol (e):
Unsaturated group-containing diol (c):
   5 to 80% by weight, preferably 10 to 70% by weight, much desirably 15 to 60% by weight;
Polyisocyanate compound (d):
   3 to 70% by weight, preferably 5 to 50% by weight, much desirably 10 to 40% by weight;
Polyol (e):
   0 to 50% by weight, preferably 5 to 40% by weight, much desirably 10 to 30% by weight.

Said urethane-forming reaction may be conducted in the absence of solvent or in a suitable inert organic solvent, normally at a temperature in a rage of about 20 to about 250° C., in particular 50 to 150° C., for about 10 minutes to about 24 hours, in particular about 20 minutes to about 12 hours.

In the above-mentioned reaction, if necessary, there may be used a known catalyst to accelerate urethane-forming reaction between isocyanate group and hydroxyl group. Examples of usable reaction catalyst include lead oleate, tetrabutyl tin, antimoy trichloride, triphenyl aluminum, trioctyl aluminum, zinc naphthenate, zirconium naphthenate, dibutyltin dilaurate, tetra-n-butyl-1,3-diacetyloxydistannoxane, 1,4-diaza[2,2,2]bicyclooctane and N-ethylmorpholine. Said reaction catalyst is desirably used in an amount of 0.01 to 10 parts by weight, preferably 0.05 to 5 parts by weight, per 100 parts by weight of total solid content of unsaturated group-containing diol (c), polyisocyanate compound (d) and polyol (e).

When thus obtained unsaturated group-containing urethane resin (A) has isocyanate group, said isocyanate group may be made to react, if necessary, with hydroxyl group-containing ethylenically unsaturated monomer (f), by which to introduce ethylenically unsaturated group at molecular chain terminals of this resin. Examples of said hydroxyl group-containing ethylenically unsaturated monomer (f) include hydroxyalkyl(meth)acrylate such as 2-hydroxyethyl (meth)acrylate, 2- or 3-hydroxypropyl(meth)acrylate and butanediol mono(meth)acrylate; N-alkanol(meth) acrylamide such as N-methylol(meth)acrylamide; ethylenically unsaturated alcohol such as allyl alcohol and crotyl alcohol; and propyleneglycol mono(meth)acrylate, trimethylolpropane di(meth)acrylate and pentaerythritol tri (meth)acrylate. Furthermore, there can be used an adduct of glycidyl(meth)acrylate with monocarboxylic acid compound (e.g., acetic acid, propionic acid and crotonic acid) or an adduct of (meth)acrylic acid with epoxy compound (e.g., epichlorohydrin). These compounds may be used either separately or in combination of two or more species. Especially suitable among the above compounds is hydroxyalkyl (meth)acrylate.

Or, when thus obtained unsaturated group-containing urethane resin (A) has hydroxyl group, said hydroxyl group may be made to react, if necessary, with isocyanate group-containing ethylenically unsaturated monomer (g), by which to introduce ethylenically unsaturated group at molecular chain terminals of this resin. Examples of said isocyanate group-containing ethylenically unsaturated monomer (g) include ethylmethacrylate isocyanate and an adduct (e.g., a mono adduct of isophorone diisocyanate with hydroxyethyl methacrylate) which is prepared by adding a monomer which has both hydroxyl group and ethylenically unsaturated group to one isocyanate group of diisocyanate compound, among which ethylmethacrylate isocyanate is especially suitable.

The above-mentioned reaction between unsaturated group-containing urethane resin (A) which has isocyanate group or hydroxyl group, and hydroxyl group- or isocyanate group-containing ethylenically unsaturated monomer (f) or (g) is desirably conducted so that NCO/OH equivalent ratio may fall within a range of 0.8/1 to 1/0.8.

Unsaturated group-containing urethane resin (A) which is produced in the above-mentioned manner may have ethylenically unsaturated groups in an amount within a range of 0.5 to 5 mol/kg, preferably 0.7 to 4 mol/kg, much desirably 1 to 3.5 mol/kg, and has a number average molecular weight generally within a range of 400 to 100,000, in particular 500 to 50,000, much desirably 1,000 to 10,000.

It is preferable that unsaturated group-containing urethane resin (A) has suitable hydrophilicity, and is capable of dispersing uniformly in aqueous medium. If necessary, hydrophilicity can be enhanced by introducing, into the urethane resin (A), ionic or nonionic hydrophilic group such as hydroxyl group, amino group, carboxyl group, phosphoric group, sulfonic group and ether bond. Among these, ether bond is most suitably introduced, since it can improve the hydrophilicity of the urethane resin (A) without decreasing adhesiveness to microbial cells.

The introduction of ether bond can be conducted by replacing, in the production of the urethane resin (A), a part of unsaturated group-containing diol (c) with polyol having ether bond such as diethylene glycol, triethylene glycol, polyethylene glycol (molecular weight: at most 6,000), dipropylene glycol and polypropylene glycol, preferably diethylene glycol, triethylene glycol and polyethylene glycol (molecular weight: at most 6,000).

Photopolymerization Initiator (B)

As polymerization initiator, i.e., component (B) in aqueous liquid composition, there are suitably employed photopolymerization initiator and/or redox type thermopolymerization initiator.

As photopolymerization initiator, any known ones can be used without particular restriction, examples of which include benzoin, benzoin methyl ether, benzoin ethyl ether, benzoin butyl ether, diethoxy acetophenone, 2-hydroxy-2-methyl-1-phenylpropan-1-one, benzylmethylketal, 1-hydroxycyclohexyl-phenylketone, 2-methyl-2-morpholino(4-thiomethylphenyl)propan-1-one, 2-benzyl-2-dimethylamino-1-(4-morpholinophenyl)-butanone, 2,4,6-trimethylbenzoyldiphenylphosphine oxide, 2,4,6-trimethylbenzoyldiphenylethoxyphosphine oxide, benzophenone, methyl o-benzoylbenzoate, hydroxybenzophenone, 2-isopropylthioxantone, 2,4-dimethylthioxantone, 2,4-diethylthioxantone, 2,4-dichlorothioxantone, 2,4,6-tris(trichloromethyl)-S-triazine, 2-methyl-4,6-bis(trichloro)-S-triazine and 2-(4-methoxyphenyl)-4,6-bis(trichloromethyl)-S-triazine. These compounds may be used either separately or in combination of two more more species.

With a view to accelerating photopolymerization reaction which is caused by these photopolymerization initiator, photosensitization accelerator may be employed together with photopolymerization initiator. Examples of usable photosensitization accelerator include tertiary amino group type ones such as triethylamine, triethanolamine, methyldiethanolamine, 4-dimethylamino isoamylbenzoate, (2-dimethylamino)ethylbenzoate, Michler's ketone and 4,4'-diethylaminobenzophenone; alkylphosphine type ones such as triphenylphosphine; and thioether type ones such as β-thioglycol. These photosensitization accelerators may be used either separately or in combination of two or more species.

As redox type thermopolymerization initiator, any known ones can be used. Suitably usable one is a polymerization initiator which is composed of oxidizing agent and reducing agent, and which is capable of causing radical polymerization at a comparatively low temperature of −10° C. to 50° C.

Examples of oxidizing agent include organic peroxides such as benzoyl peroxide, methylethylketone peroxide, dicumyl peroxide, t-butyl perbenzoate and cumene hydroperoxide; peroxodisulfate such as ammonium peroxodisulfate and potassium peroxodisulfate; and hydrogen peroxide.

Examples of reducing agent include hydrogensulfites such as sodium hydrogensulfite; divalent iron salts such as ferrous sulfate and ferrous chloride; amines such as N,N-dimethylaniline and phenylmorpholine; and metal salts of naphthenic acid such as cobalt naphthenate, manganese naphthenate and copper naphthenate.

Redox type thermopolymerization initiator is used as a combination of oxidizing agent and reducing agent. These two components are suitably mixed in a molar ratio within a range of 5:1 to 1:5, preferably 2.5:1 to 1:2.5. Photopolymerization initiator and redox type thermopolymerization initiator may be used in combination.

Water-soluble Macromolecular Polysaccharides (C)

Water-soluble macromolecular polysaccharides which are to be used in this invention are macromolecular polysaccharides which are capable of changing into gel either insoluble or hardly soluble in water when brought into contact with metal ion in an aqueous medium, and which, in general, have a number average molecular weight in a range of about 3,000 to 2,000,000, especially 5,000 to 200,000, and which usually show a solubility of at least about 10 g/l (25° C.), especially at least about 20 g/l (25° C.), in a water-soluble state before brought into contact with metal ion.

Examples of water-soluble macromolecular polysaccharides which have such properties include alkali metal salt of alginic acid and carageenan. These water-soluble macromolecular polysaccharides are, in a state as dissolved in an aqueous medium, capable of gelation by contact, in the case of carageenan, with alkali metal ion such as potassium ion or sodium ion, or, in the case of alkali metal salt of alginic acid, by contact with at least one polyvalent metal ion such as magnesium ion, calcium ion, strontium ion, barium ion, aluminum ion, cerium ion and nickel ion. The concentration of alkali metal ion or polyvalent metal ion at which gelation occurs differs depending on the species of water-soluble macromolecular polysaccharides etc. Generally, however, the concentration of these metal ions is in a range of 0.01 to 5 mol/l, in particular 0.1 to 1 mol/l. These water-soluble macromolecular polysaccharides may be used either separately or in combination of two or more species.

Aqueous Liquid Composition

Aqueous liquid composition can be prepared by mixing the above-mentioned unsaturated group-containing urethane resin (A), polymerization initiator (B) and water-soluble macromolecular polysaccharides (C). The proportion among the above-mentioned components (A), (B) and (C) is not strictly restricted, but may be varied widely according to the species of the components. Generally, however, components (B) and (C) are preferably used in the following ratio based on 100 parts by weight of unsaturated group-containing urethane resin (A):

Polymerization initiator (B):

0.1 to 10 parts by weight, preferably 0.3 to 7 parts by weight, in particular 0.5 to 5 parts by weight;

Water-soluble macromolecular polysaccharides (C):

0.5 to 15 parts by weight, preferably 1 to 10 parts by weight, in particular 2 to 5 parts by weight.

Molded particles which are produced from an aqueous liquid composition which in turn is formed substantially only from the above-mentioned urethane resin (A), polymerization initiator (B) and water-soluble macromolecular polysaccharides (C) have generally a specific gravity of 1.00 to 1.03, i.e., almost the same as that of water. The specific gravity can, however, be adjusted to any desired value by means of adding a specific gravity adjustor such as pigment and hollow particles. When specific gravity is desired to be increased, a specific gravity adjustor which have a specific gravity of 1 or more such as glass beads, talc, mica and baryta is added in an amount of 0.1 to 50 parts by weight per 100 parts by weight of the above-mentioned urethane resin (A), so that molded particles may have a specific gravity within a range of 1.00 to 1.25. When, on the other hand, specific gravity is desired to be decreased, a specific gravity adjustor such as hollow glass beads, hollow Celite and hollow polymer which have a specific gravity of 1 or less is added in an amount of 0.1 to 30 parts by weight per 100 parts by weight of the above-mentioned urethane resin (A), so that molded particles may have a specific gravity within a range of 0.90 to 1.00.

The above-mentioned components (A), (B) and (C), and a specific gravity adjustor which is to be added as circumstances may demand, are dissolved or dispersed in an aqueous medium, and, thus, an aqueous liquid composition is prepared. The soild content of this aqueous liquid composition is suitably within a range of 5 to 30% by weight.

When redox type thermopolymerization initiator is used as a polymerization initiator, both an oxidizing agent and a reducing agent may simultaneously be included in aqueous liquid composition. It is also acceptable, however, to include only one of oxidizing agent and reducing agent in aqueous liquid composition, while including the other in a metal ion-containing aqueous medium in a concentration of 0.05 to 5% by weight, preferably 0.1 to 2% by weight.

Production of Molded Particles

Thus prepared aqueous liquid composition is then dripped into such a metal ion-containing aqueous medium as mentioned above. Otherwise, when it is desired to obtain particles whose average particle size is 5 mm or more, the aqueous liquid composition is poured onto the surface of said aqueous medium continuously for a predetermined time so that droplet may grow to a desired size, and, then, the droplet is precipitated. In this manner, said aqueous liquid composition is gelatinized into granule.

The dripping of aqueous liquid composition into a metal ion-containing aqueous medium is conducted by dripping said aqueous liquid composition from the tip of syringe, or by scattering said aqueous liquid composition in the form of granules with use of centrifugal force, or by atomizing, from the tip of spray nozzle, said aqueous liquid composition to be granulated and dripped. When, on the other hand, the aqueous liquid composition is to be poured onto the surface of said aqueous medium, it can be carried out by continuously supplying the aqueous liquid composition as a thin liquid stream from a nozzle of a desired bore. The size of droplets which are thus dripped may be varied optionally according to the particle size which is required of final particles for immobilization. Usually, however, it is convenient that the droplet has a diameter of about 0.1 mm to about 5 mm, preferably about 0.5 mm to about 4 mm. When the aqueous liquid composition is to be poured, on the other hand, the droplet has conveniently a diameter of about 0.5 mm to 3 mm.

Thus formed granular gel is, either in a state of dispersion in the aqueous medium or after separated from the aqueous medium, subjected to photopolymerization or thermopolymerization, and, thus, urethane resin in said granular gel can be cured. The granular gel thereby makes molded particles for microbial cell-immobilization which are substantially insoluble in water and have large mechanical strength.

When the above-mentioned curing is to be conducted by means of photopolymerization, the wave length of active ray to be used differs according to the species of urethane resin which is contained in said granular gel. Generally, however, an illuminant which emits light having a wave length in a range of about 250 to about 600 nm, in particular 250 to 400 nm, is advantageously used. Examples of such an illuminant include low-pressure mercury lamp, high-pressure mercury lamp, fluorescent lamp, xenon lamp, carbon-arc lamp and sun light. Irradiation time needs to be changed according to the intensity of light from the illuminant and the distance from the illuminant. Generally, it may be in a range of about 0.5 to about 10 minutes.

When the curing of urethane resin is carried out by thermopolymerization, granular gel, so long as it contains redox type thermopolymerization initiator, proceeds with thermopolymerization until necessary mechanical strength is obtained, if only left to stand still at room temperature. Where appropriate, however, granular gel may be heat-cured. Curing temperature is preferably within a range of 0 to 50° C., in particular 20 to 40° C. In order that necessary mechanical strength may be achieved, it is desirable to spend at least 10 to 30 minutes for heat-curing.

Granular gel which has thus been subjected to photopolymerization and/or thermopolymerization is washed with water or aqueous buffer solution, and may be stored as it is, or after freeze dried.

The molded particles for enzyme- or microbial cell-immobilization which are produced by this invention have a surface structure which is especially suitable for the adhesion of enzymes or microorganisms, and, therefore, allow a large amount of enzymes or microorganisms to adhere thereto. Examples of enzyme which may be made to adhere to said carrier include lipase, amylase, protease, cellulase, pectinase, invertase and lactase. Both anaerobic and aerobic microorganisms are acceptable as microorganism to adhere to this carrier. Examples of such microorganisms include molds such as genus *Aspergillus*, genus *Penicillium* and genus *Fusarium*; yeasts such as genus *Saccharomyces*, genus *Phaffia* and genus *Candida*; bacteria such as genus *Zymomonas*, genus *Pseudomonas*, genus *Nitrosomonas*, genus *Nitrobacter*, genus *Paracoccus*, genus *Vibrio*, genus *Methanosarcina* and genus *Bacillus*. The molded particles which are produced by this invention achieve large effects especially in the improvement of adhesion to microorganisms such as genus *Pseudomonas*, genus *Nitrosomonas*, genus *Nitrobacter* and genus *Paracoccus*.

When urethane resin has a curing temperature as low as room temperature, the above-mentioned enzymes or microorganisms may previously be mixed, for the sake of immobilization by encapsulation, in an aqueous liquid matter which is composed of components (A), (B) and (C).

Thus, the process of this invention for the production of molded particles for immobilization gives immobilizing particles which have large strength, and are excellent in adhesion to enzymes or microbial cells. The molded particles which are provided by the process of this invention are also applicable to bioreactor and fermentation bath.

EXAMPLES

In the following, this invention is explained in more detail by working examples, which nevertheless do not restrict this invention. In the following Examples and Comparative Examples, "parts" and "%" are based on weight.

Production of Aqueous Solution of Unsaturated Group-containing Urethane Resin

Production Example 1

A four-necked flask was fed with 500 parts of toluene, 74 parts of glycidol, 72 parts of acrylic acid, 1 part of tetraethylammonium bromide and 1 part of hydroquinone. The resultant mixture was stirred with aeration, and was then kept at a temperature of 100° C. for 10 hours for reaction, and, thus, a solution of unsaturated group-containing diol was obtained. To this solution, 1,000 parts of polyethylene glycol (average molecular weight: about 1,000) and 666 parts of isophorone diisocyanate were added, and stirred with aeration, and, then, the resulting mixture was maintained at 100° C. for eight hours for reaction, and, thus, a solution of isocyanate group-containing urethane resin was obtained. Furthermore, 232 parts of 2-hydroxyethyl acrylate was introduced into reactor, and the resultant mixture was allowed to react at 80° C. for three hours with aeration. After it was confirmed that almost no isocyanate group remained, 2,040 parts of deionized water was added and stirred well, and, then, reaction bath was vacuumized with a vacuum pump for one hour with temperature kept at 70° C. so that toluene might be removed, and, thus, there was obtained aqueous solution (A1) of unsaturated group-containing urethane resin having a solid content of about 50%. Said resin had a number average molecular weight of 2,040, and a content of ethylenically unsaturated group of 1.47 moles/kg.

Production Example 2

A four-necked flask was fed with 1,000 parts of toluene, 256 parts of epoxidized tetrahydrobenzylalcohol, 144 parts of acrylic acid, 2 parts of tetraethylammonium bromide and 2 parts of hydroquinone. The resultant mixture was stirred with aeration, and was then kept at a temperature of 100° C. for 10 hours for reaction, and, thus, a solution of unsaturated group-containing diol was obtained. To this solution, 600 parts of polyethylene glycol (average molecular weight: about 600) and 444 parts of isophorone diisocyanate were added, and stirred with aeration, and, then, the resulting mixture was maintained at 100° C. for eight hours for reaction, and, thus, a solution of hydroxyl group-containing urethane resin was obtained. Furthermore, 310 parts of ethylmethacrylate isocyanate was introduced into reactor, and the resultant mixture was allowed to react at 80° C. for three hours with aeration. After it was confirmed that almost no isocyanate group remained, 1,750 parts of deionized water was added and stirred well, and, then, reaction bath was vacuumized with a vacuum pump for one hour with temperature kept at 70° C. so that toluene might be removed, and, thus, there was obtained aqueous solution (A2) of unsaturated group-containing urethane resin having a solid content of about 50%. Said resin had a number average molecular weight of 1,750, and a content of ethylenically unsaturated group of 2.29 moles/kg.

Production Example 3

A four-necked flask was fed with 500 parts of toluene, 296 parts of glycidol, 288 parts of acrylic acid, 4 parts of tetraethylammonium bromide and 4 parts of hydroquinone. The resultant mixture was stirred with aeration, and was then kept at a temperature of 100° C. for 10 hours for reaction, and, thus, a solution of unsaturated group-containing diol was obtained. To this solution, 2,000 parts of polyethylene glycol (average molecular weight: about 2,000) and 1,044 parts of tolylene diisocyanate were added, and stirred with aeration, and, then, the resulting mixture was maintained at 100° C. for eight hours for reaction, and, thus, a solution of isocyanate group-containing urethane resin was obtained. Furthermore, 232 parts of 2-hydroxyethyl acrylate was introduced into reactor, and the resultant mixture was allowed to react at 80° C. for three hours with aeration. After it was confirmed that almost no isocyanate group remained, 3,860 parts of deionized water was added and stirred well, and, then, reaction bath was vacuumized with a vacuum pump for one hour with temperature kept at 70° C. so that toluene might be removed, and, thus, there was obtained aqueous solution (A3) of unsaturated group-containing urethane resin having a solid content of about 50%. Said resin had a number average molecular weight of 3,860, and a content of ethylenically unsaturated group of 1.55 moles/kg.

Comparative Production Example 1

A four-necked flask was fed with 700 parts of toluene, 2,000 parts of polyethylene glycol (average molecular weight: about 2,000) and 444 parts of isophorone diisocyanate, and, then, the resultant mixture was stirred, and was allowed to react at 80° C. for two hours, and, thus, an isocyanate group-containing urethane resin was obtained. Furthermore, 232 parts of 2-hydroxyethyl acrylate and 2 parts of hydroquinone were introduced into reactor, and the resultant mixture was allowed to react at 80° C. for three hours with aeration. After it was confirmed that almost no isocyanate group remained, 2,700 parts of deionized water was added and stirred well, and, then, reaction bath was vacuumized with a vacuum pump for one hour with temperature kept at 70° C. so that toluene might be removed, and, thus, there was obtained aqueous solution (A4) of ethylenically unsaturated group-containing urethane resin having a solid content of about 50%. Said resin had a number average molecular weight of 2,700, and a content of ethylenically unsaturated group of 0.74 mole/kg.

Comparative Production Example 2

A four-necked flask was fed with 600 parts of toluene, 1,200 parts of polyethylene glycol (average molecular weight: about 600) and 666 parts of isophorone diisocyanate, and, then, the resultant mixture was allowed to react at 80° C. for two hours, and, thus, an isocyanate group-containing urethane resin solution was obtained. Furthermore, 232 parts of 2-hydroxyethyl acrylate and 2 parts of hydroquinone were introduced into reactor, and the resultant mixture was allowed to react at 80° C. for three hours with aeration. After it was confirmed that almost no isocyanate group remained, 2,100 parts of deionized water was added and stirred well, and, then, reaction bath was vacuumized with a vacuum pump for one hour with temperature kept at 70° C. so that toluene might be removed, and, thus, there was obtained aqueous solution (A5) of ethylenically unsaturated group-containing urethane resin having a solid content of about 50%. Said resin had a number average molecular weight of 2,100, and a content of ethylenically unsaturated group of 0.95 mole/kg.

Example 1

An aqueous liquid composition, which had been prepared by well-mixing 100 parts of aqueous solution (A1) of urethane resin of Production Example 1, 2 parts of benzoin isobutylether, 50 parts of distilled water and 100 parts of 2% aqueous solution of sodium alginate, was dripped into 5% aqueous solution of calcium chloride from the tip of syringe which was about 10 cm above liquid surface, and, thus, there were obtained particulate matters having a particle size of about 2 mm. Said particulate matters were placed on a petri dish, which was then irradiated, for 30 seconds, from both upper and under sides with ultraviolet ray emitted from a high-pressure mercury lamp, and, thus, molded particles were obtained.

Example 2

An aqueous liquid composition, which had been prepared by well-mixing 100 parts of aqueous solution (A2) of urethane resin of Production Example 2, 1 part of ammonium peroxodisulfate, 1 part of sodium bisulfite, 50 parts of distilled water and 100 parts of 2% aqueous solution of sodium alginate, was dripped into 5% aqueous solution of calcium chloride from the tip of syringe which was about 10 cm above liquid surface, and, thus, there were obtained particulate matters having a particle size of about 2 mm. Said particulate matters were left to stand still as they were at 30° C. for 30 minutes, and, thus, molded particles were obtained.

Example 3

An aqueous liquid composition, which had been prepared by well-mixing 100 parts of aqueous solution (A3) of urethane resin of Production Example 3, 2 parts of benzoin isobutylether, 1 part of ammonium peroxodisulfate, 1 part of sodium bisulfite, 50 parts of distilled water and 100 parts of 2% aqueous solution of sodium alginate, was dripped into 5% aqueous solution of calcium chloride from the tip of syringe which was about 10 cm above liquid surface, and, thus, there were obtained particulate matters having a particle size of about 2 mm. Said particulate matters were placed on a petri dish, which was then irradiated, for 30 seconds, from both upper and under sides with ultraviolet ray emitted from a high-pressure mercury lamp, and was then left to stand still at 30° C. for 30 minutes, and, thus, molded particles were obtained.

Comparative Example 1

Molded particles were obtained in the same manner as in Example 1 except that aqueous solution (A1) of urethane resin used in Example 1 was replaced with aqueous solution (A4) of urethane resin of Comparative Production Example 1.

Comparative Example 2

Molded particles were obtained in the same manner as in Example 2 except that aqueous solution (A2) of urethane resin used in Example 2 was replaced with aqueous solution (A5) of urethane resin of Comparative Production Example 2.

Molded particles which had been produced according to the above-mentioned Examples and Comparative Examples were measured for compressive strength and adherability to microbial cell. Results are shown in Table 1 below.

Test Method

Compressive Strength

Pressure at which molded particles were destroyed was determined by EZ TEST of Shimadzu Seisakusho K. K.

Adherability to Microbial Cell

Molded particles were each placed in a 500-ml conical flask, into which 100 ml of GY-10 medium (composed of 1 g/l of yeast extract and 100 g/l of glucose) was subsequently poured. To the resultant mixture, *Zymomonas mobilis* IFO 13756 at a concentration of 2% was added, and was subjected to stationary activation culturing at 30° C. for 24 hours. After activation was over, the surface of each molded particles for immobilization was washed with distilled water, and activated fermentation liquid was replaced with new medium, which, in turn, was subjected to stationary culturing for 24 hours, and, then, the concentration of ethanol was determined.

TABLE 1

|  |  | Examples | | | Comparative Examples | |
|---|---|---|---|---|---|---|
|  |  | 1 | 2 | 3 | 1 | 2 |
| Characteristics | Particle size (mm) | 2.1 | 2.2 | 2.1 | 2.2 | 2.1 |
|  | Specific density | 1.03 | 1.02 | 1.03 | 1.02 | 1.02 |
| Test Results | Compressive strength (kg/cm$^2$) | 38 | 43 | 45 | 21 | 19 |
|  | Adherability to microbial cell (ethanol concentration, %) | 7 | 7.1 | 6.9 | 6.9 | 7.1 |

As is clearly seen in the above results, molded particles which are produced by the method of this invention are of very high mechanical strength and are excellent in adherability to enzyme and microbial cell.

What is claimed is:

1. A process for the production of molded particles for enzyme- or microbial cell-immobilization wherein:
   an aqueous liquid composition which comprises:
   (A) an unsaturated group-containing urethane resin which is obtained by making a compound (a) having one hydroxyl group and one epoxy group in a molecule react with a compound (b) having one carboxyl group and one ethylenically unsaturated group in a molecule, and further making thus obtained unsaturated group-containing diol (c) react with polyisocyanate compound (d);
   (B) a polymerization initiator; and
   (C) water-soluble macromolecular polysaccharides which are capable of gelation by contact with metal ion;
   is gelatinized, in an aqueous medium which contains metal ion, to be particulate gel, which is then subjected to photopolymerization and/or thermopolymerization by which to cause the crosslinking reaction of ethylenically unsaturated group in said particulate gel.

2. The process of claim 1 wherein compound (a) is selected from the group consisting of glycidol and a compound of the following formula (I) or (II):

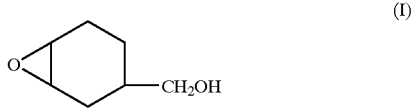

(I)

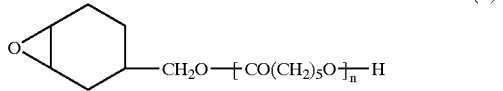

(II)

wherein n denotes an integer of 1 to 10, preferably 1 to 3.

3. The process of claim 1 wherein compound (a) is glycidol.

4. The process of claim 1 wherein compound (b) is selected from the group consisting of acrylic acid, methacrylic acid, ω-carboxy-polycaprolactone monoacrylate, phthalic acid monohydroxyethyl acrylate, acrylic acid dimer, phthalic acid monohydroxypropyl acrylate, hexahydrophthalic acid monohydroxypropyl acrylate and tetrahydrophthalic acid monohydroxypropyl acrylate.

5. The process of claim 1 wherein compound (b) is acrylic acid or methacrylic acid.

6. The process of claim 1 wherein polyisocyanate compound (d) is diisocyanate compound.

7. The process of claim 1 wherein polyisocyanate compound (d) is selected from the group consisting of tolylene diisocyanate, 4,4'-diphenylmethane diisocyanate, xylylene diisocyanate, hexamethylene diisocyanate, isophorone diisocyanate, trimethylhexamethylene diisocyanate and dimer acid diisocyanate.

8. The process of claim 1 wherein unsaturated group-containing diol (c) is partially replaced with other polyol (e).

9. The process of claim 8 wherein other polyol (e) is selected from the group consisting of diethylene glycol, triethylene glycol and polyethylene glycol which has a molecular weight of at most 6,000.

10. The process of claim 1 or 8 wherein unsaturated group-containing urethane resin (A) is produced from a reaction among 5 to 80% by weight of unsaturated group-containing diol (c), 3 to 70% by weight of polyisocyanate compound (d) and 0 to 50% by weight of polyol (e), on the basis of total solid content of unsaturated group-containing diol (c), polyisocyanate compound (d) and polyol (e).

11. The process of claim 1 wherein unsaturated group-containing urethane resin (A) has a content of ethylenically unsaturated groups in an amount within a range of 0.5 to 5 mol/kg.

12. The process of claim 1 wherein unsaturated group-containing urethane resin (A) has a number average molecular weight within a range of 400 to 50,000.

13. The process of claim 1 wherein polymerization initiator (B) is selected from the group consisting of photopolymerization initiator and redox type thermopolymerization initiator.

14. The process of claim 1 wherein water-soluble macromolecular polysaccharides (C) are selected from the group consisting of alkali metal alginate and carageenan.

15. The process of claim 1 wherein water-soluble macromolecular polysaccharides (C) are carageenan and wherein metal ion is alkali metal ion.

16. The process of claim 1 wherein water-soluble macromolecular polysaccharides (C) are alkali metal alginate and wherein metal ion is polyvalent metal ion.

17. The process of claim 1 wherein aqueous liquid composition comprises 0.1 to 10 parts by weight of polymerization initiator (B) and 0.5 to 15 parts by weight of water-soluble macromolecular polysaccharides (C) per 100 parts by weight of unsaturated group-containing urethane resin (A).

18. Molded particles which have been produced by the process of claim 1.

19. Molded particles having enzymes or microbial cells immobilized thereon, which have been produced by the process of claim 1.

20. The process of claim 1, wherein the polymerization initiator (B) is a redox thermopolymerization initiator comprising an oxidizing agent and a reducing agent, wherein either the oxidizing agent or reducing agent exist in the aqueous liquid composition and the other existing in the metal ion-containing aqueous medium.

* * * * *